(12) United States Patent
Whitsett

(10) Patent No.: US 8,728,158 B2
(45) Date of Patent: May 20, 2014

(54) EXCHANGEABLE INTRAOCULAR LENS DEVICE AND METHOD OF USE

(76) Inventor: Jeffrey C. Whitsett, Houston, TX (US)

( * ) Notice: Subject to any disclaimer, the term of this patent is extended or adjusted under 35 U.S.C. 154(b) by 891 days.

(21) Appl. No.: 12/658,430

(22) Filed: Feb. 9, 2010

(65) Prior Publication Data

US 2010/0204790 A1 Aug. 12, 2010

Related U.S. Application Data

(60) Provisional application No. 61/207,101, filed on Feb. 9, 2009.

(51) Int. Cl.
*A61F 2/16* (2006.01)

(52) U.S. Cl.
USPC ......... 623/6.43; 623/6.39; 623/6.4; 623/6.41; 623/6.44

(58) Field of Classification Search
USPC ................................................ 623/6.43, 6.44
See application file for complete search history.

(56) References Cited

U.S. PATENT DOCUMENTS

| 4,434,515 | A * | 3/1984 | Poler ............................. 623/6.41 |
| 6,797,004 | B1 | 9/2004 | Brady et al. |
| 6,960,231 | B2 | 11/2005 | Tran |
| 6,972,034 | B2 | 12/2005 | Tran et al. |
| 7,175,661 | B1 | 2/2007 | Chung et al. |
| 7,462,194 | B1 | 12/2008 | Blake |
| 7,569,073 | B2 | 8/2009 | Vaudant et al. |
| 2002/0173846 | A1 | 11/2002 | Blake et al. |
| 2003/0149480 | A1 | 8/2003 | Shadduck |
| 2004/0111152 | A1 | 6/2004 | Kelman |
| 2004/0249455 | A1 | 12/2004 | Tran |
| 2005/0015145 | A1 | 1/2005 | Tran et al. |
| 2005/0209692 | A1 | 9/2005 | Zhang |
| 2005/0246019 | A1 | 11/2005 | Blake et al. |
| 2005/0273163 | A1 | 12/2005 | Tran et al. |
| 2006/0047339 | A1 | 3/2006 | Brown |
| 2006/0116765 | A1 | 6/2006 | Blake et al. |
| 2006/0235515 | A1 * | 10/2006 | Chassain ...................... 623/6.16 |
| 2008/0125862 | A1 | 5/2008 | Blake et al. |
| 2008/0161912 | A1 * | 7/2008 | Scott ............................ 623/6.11 |

FOREIGN PATENT DOCUMENTS

EP PCT/FR1999/002446 4/2000
EP 1 138 282 A1 10/2001

* cited by examiner

*Primary Examiner* — David Isabella
*Assistant Examiner* — Joshua Levine
(74) *Attorney, Agent, or Firm* — Stinson Leonard Street LLP

(57) ABSTRACT

An exchangeable intraocular lens device having a flexible, high-memory expansile lens fixation platform adapted to receive the haptics of an intraocular lens, and their method of use, are provided. The device is specifically designed to expand completely into the equatorial fornix of the capsular bag and become permanently implanted therein. The design of the present invention addresses the desire of patients to exchange their existing intraocular lens to meet their changing visual needs or to take advantage of improved lens technology, without incurring the significant risks typically associated with exchange of current intraocular lens technology. The exchangeable intraocular lens device provides accurate centration, positioning, and stability of the intraocular lens in the capsular bag. The exchangeable intraocular lens device reduces lens epithelial cell migration and resultant posterior capsule opacification.

19 Claims, 11 Drawing Sheets

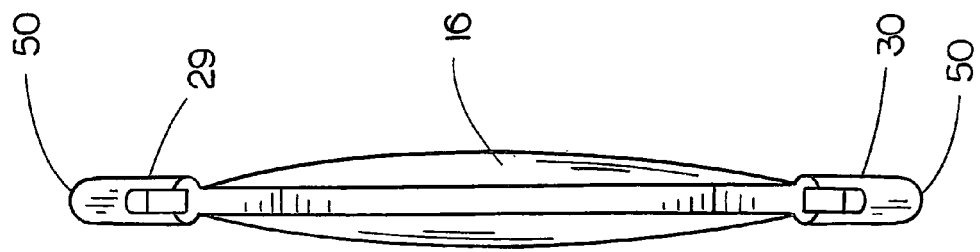
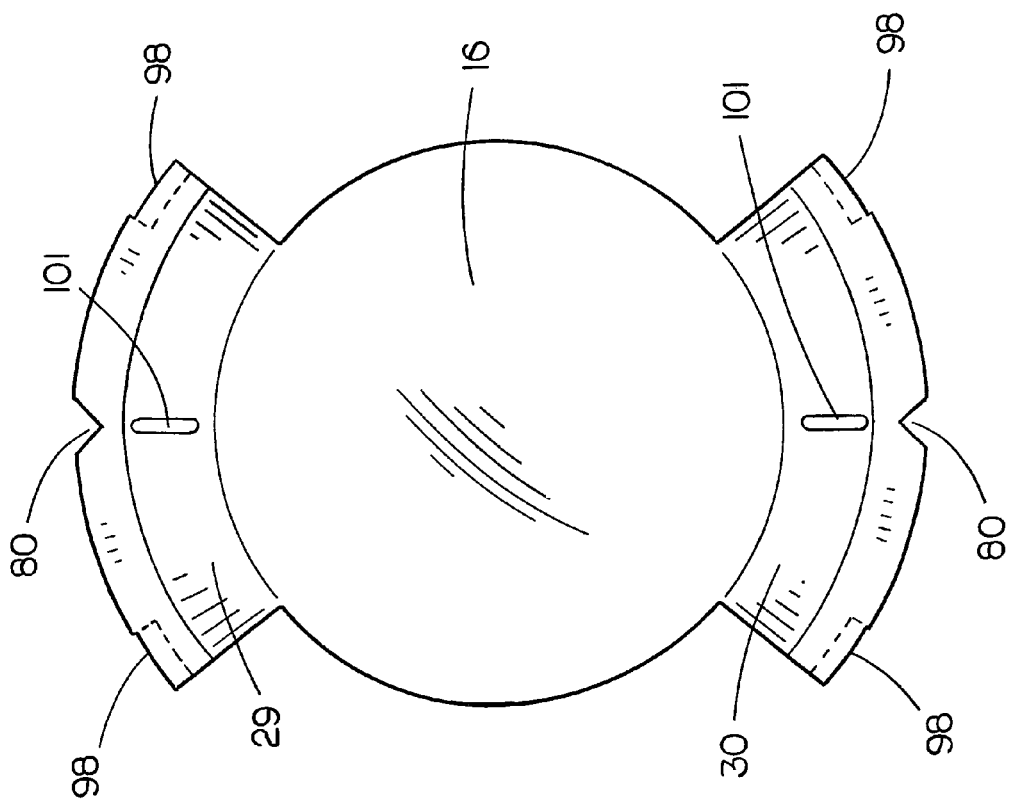
FIG. 6B
FIG. 6A

EXCHANGEABLE INTRAOCULAR LENS DEVICE AND METHOD OF USE

CROSS-REFERENCE TO RELATED APPLICATIONS

This application is based on and claims priority to U.S. Provisional Application Ser. No. 61/207,101, filed on Feb. 9, 2009 which is hereby incorporated herein in its entirety by reference.

STATEMENT REGARDING FEDERALLY SPONSORED RESEARCH OR DEVELOPMENT

Not applicable.

BACKGROUND OF THE INVENTION

1. Field of the Invention

The present invention is directed generally to the field of intraocular lenses, and, more specifically, to an exchangeable lens fixation platform for an intraocular lens, an intraocular lens specifically designed for use with the platform, and the combination of platform and intraocular lens and its method of use.

2. Background

Current intraocular lenses often include an optically clear lens and flexible haptics which extend from the lens in various configurations and securely seat the lens in the capsular bag of the eye. As such, tissue growth and fibrosis, occurs around the haptics and "glue" these intraocular lenses in place, over time. As a result, current intraocular lenses cannot be removed without causing potential damage to the eye and possibly blindness.

Intraocular lenses are clear, resiliently deformable, i.e., capable of being rolled or folded onto itself, lens that focus light onto the retina and may be inserted into the natural lens compartment or capsular bag of the eye, for example after removal of the natural lens during cataract surgery. Intraocular lenses often include a lens body, referred to as an 'optic', having an optically clear lenses, and flexible fixation members, referred to as 'haptics'. With most current intraocular lenses, the haptics extend from the optic to seat the lens in the capsular bag and become fibrosed within the bag. The history of intraocular lenses is one of steady progress, however the progress has been the result of design improvement after careful observation of surgical results of new designs. Historically, intraocular lenses when placed appropriately become fibrosed into position by the eye's healing mechanisms. This has allowed intraocular lenses to be recentered, or removed and replaced very early in the post-operative period. However, when the fibrosing of the ocular structures is mature (usually 6-12 months) the intraocular lens is unable to be removed without the patients visual result, and ocular health, at significant risk. The late removal of a fully healed intraocular lens could possibly result in damage to the capsular bag severe enough to be unable to place a new intraocular lens. An intraocular lens which was placed into the capsular bag years previously cannot be removed for multiple reasons. The fibrotic capsule simply claims the intraocular lens as its own, and upon attempted removal the structure would be damaged. The zonules, support structures connecting the ciliary body with the capsular bag, would likely be damaged upon traumatic intraocular lens removal, making the replacement of a lens extremely difficult. With use of prior art intraocular lenses, YAG laser capsulotomies may need to be performed to "open" a capsule which has become opacified. Attempting to exchange prior art intraocular lenses after a YAG capsulotomy is contraindicated unless the patient has a sight threatening condition.

Ophthalmic microsurgical innovations have allowed great improvements in corneal as well as intraocular lens surgical techniques. As a result, the ability to enhance a patient's surgical outcome by adjusting an intraocular lens after the procedure would be welcomed. After corneal surgery (penetrating keratoplasty, lamellar keratoplasty, DSEK (descemet's stripping endothelial keratoplaty)), there is often a significant shift in the patients refractive system. An intraocular lens which may have been pre-operatively appropriate for the patient, may indeed limit their visual result post-operatively. Therefore, it would be of particular value to be able to adjust the post-operative result by testing for stability, and subsequently exchanging their intraocular lens fora design which will improve their visual result. Surgically induced astigmatism, hyperopia, myopia, may all be augmented by intraocular lens exchange as further corneal surgery would best be avoided.

Throughout life our ocular health, and visual performance is a dynamic process. Many patients develop conditions throughout life which may affect their ocular health. Patients who have significant family history of progressive ocular diseases (age related macular degeneration, glaucoma, diabetes, Fuch's endothelial dystrophy) may only manifest the disease and its ocular side effects years after they have had intraocular lens surgery. An intraocular lens which may have been appropriate at the time of initial surgery, may indeed become a detriment if the patient develops a progressive ocular condition. Patients with a progressive ocular condition may not benefit from multifocal technology, and possibly their visual result may worsen because of this combination. The ability to safely exchange an intraocular lens based on a patient's ocular health, probability for their condition to progress, would be of assistance in allowing them to obtain their best functioning vision.

Historically intraocular lens systems have encouraged surgeons to implant the best technology presently available, knowing there may be significant risks associated with attempted removal of the IOL. These risks limit the ability to adjust or exchange an IOL to take advantage of future developments in lens technology in order to meet patient's changing needs and improve their visual results. There is, therefore, a need for an exchangeable intraocular lens device which enables a patient to exchange their existing intraocular lens for a new or superior intraocular lens. The present invention meets these needs.

BRIEF SUMMARY OF THE INVENTION

The present invention is directed to an intraocular lens device having a ring-shaped lens fixation platform which is injected into an evacuated intracapsular bag of an eye. The platform has attachments for exchangeably receiving an intraocular lens. The intraocular lens includes an optic with integral haptics that are specifically adapted to fit securely in the attachments on the lens fixation platform. The novel design of the intraocular lens device makes possible a method to subsequently remove an intraocular lens and exchange it for a new intraocular lens of the same haptic design.

More specifically, one embodiment of the present invention provides a generally ring-shaped lens fixation platform made of biocompatible, flexible, high memory material, such as acrylic. After insertion through a small corneal incision into the evacuated capsular bag of an eye, the platform expands along its complete circumference to fit securely into the fornix of the capsular bag. The lens fixation platform adheres to the fornix and becomes permanently implanted in the capsular bag. The lens fixation platform of the present invention creates a "frame" to which the intraocular lens of the present invention can be attached, and from which the intraocular lens can be disengaged if it becomes desirable to remove or replace the intraocular lens. The lens fixation platform includes two or more attachments which project from the interior of the lens fixation platform inward toward the center axis of the ring-shaped lens fixation platform. The inner most margin of each attachment is configured to engage the haptics of an intraocular lens. The lens fixation platform may have one or more circumferential ridges on the posterior surface and may have a convex anterior surface. There may be one or more alignment guides on the lens fixation platform.

Another embodiment of the present invention provides an intraocular lens including an optic, which provides all of the desired corrective lens power, and two or more integral haptics which extend outward from the periphery of the optic. The intraocular lens is specifically adapted to fit within the lens fixation platform, similar to a picture in a frame. To accomplish this, the haptics are spaced and the peripheral margins of the haptics are specifically adapted to engage the inner most margins of the attachments on the lens fixation platform. The peripheral margins of the haptic may have one or more disengagement means to facilitate subsequent removal of the intraocular lens from the lens fixation platform.

A further embodiment of the present invention provides an exchangeable intraocular lens device comprised of the lens fixation platform and intraocular lens which are assembled after being inserted into an evacuated capsular bag of an eye.

The discovery of the present invention makes possible a surgical method for insertion and subsequent removal and exchange of an intraocular lens with reduced risk of injury to the eye or loss of sight.

BRIEF DESCRIPTION OF THE DRAWINGS

All measurements noted on the drawings are in millimeters and dimensions are in degrees of arc.

FIG. 3A is an enlarged sectional side view of FIG. 2C at circle a.

FIG. 3B is an enlarged sectional side view of FIG. 2C at circle b.

FIG. 6A is a front/anterior view of the intraocular lens.

FIG. 6B is a side view of the intraocular lens of FIG. 6A.

DETAILED DESCRIPTION OF PREFERRED EMBODIMENT

Figure 2:
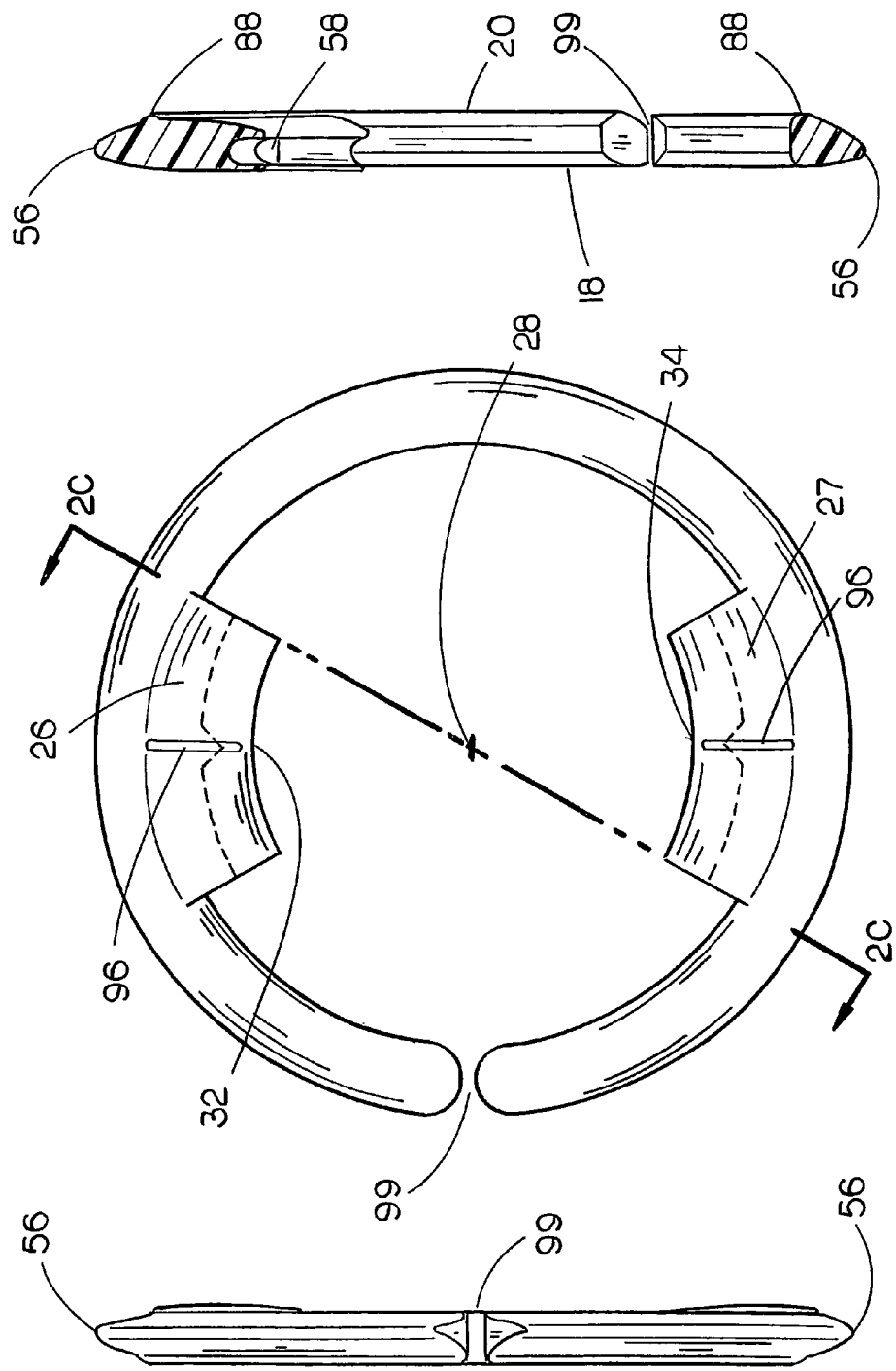
FIG. 2A is a left side view of the lens fixation platform of FIG. 2B.
FIG. 2B is an anterior view of the lens fixation platform.
FIG. 2C is a sectional side view of the lens fixation platform taken along line c-c in FIG. 2B.
Figure 7B:
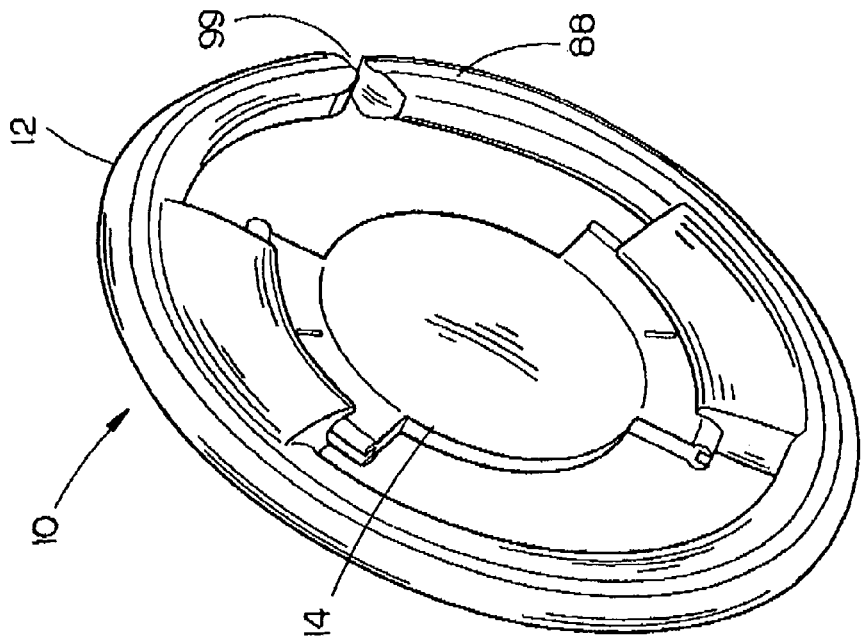
FIG. 7B is a rear/posterior view of the assembled lens fixation platform and intraocular lens of the exchangeable intraocular lens device.
Figure 7A:
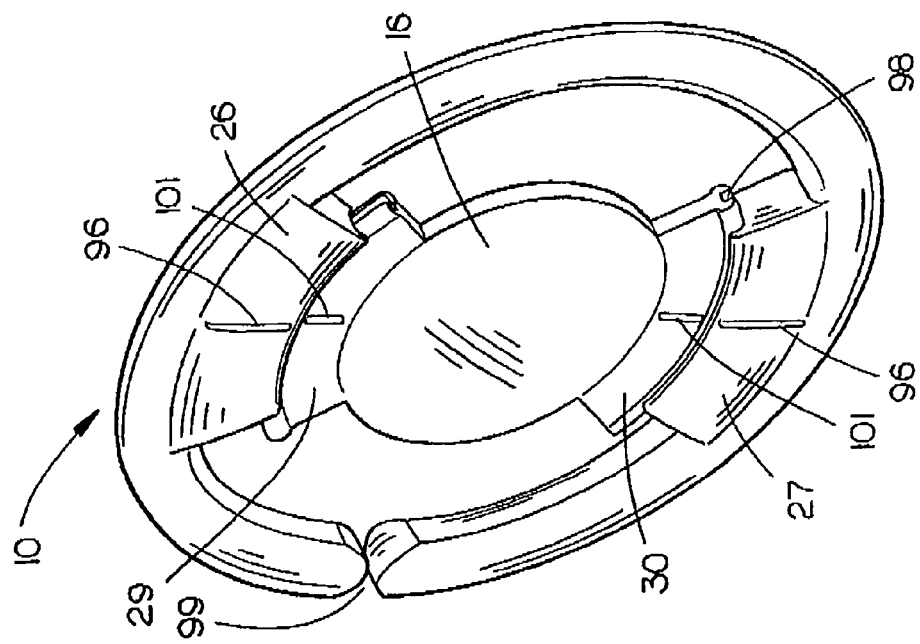
FIG. 7A is a front/anterior view of the assembled lens fixation platform and intraocular lens of the exchangeable intraocular lens device.
Figure 9:
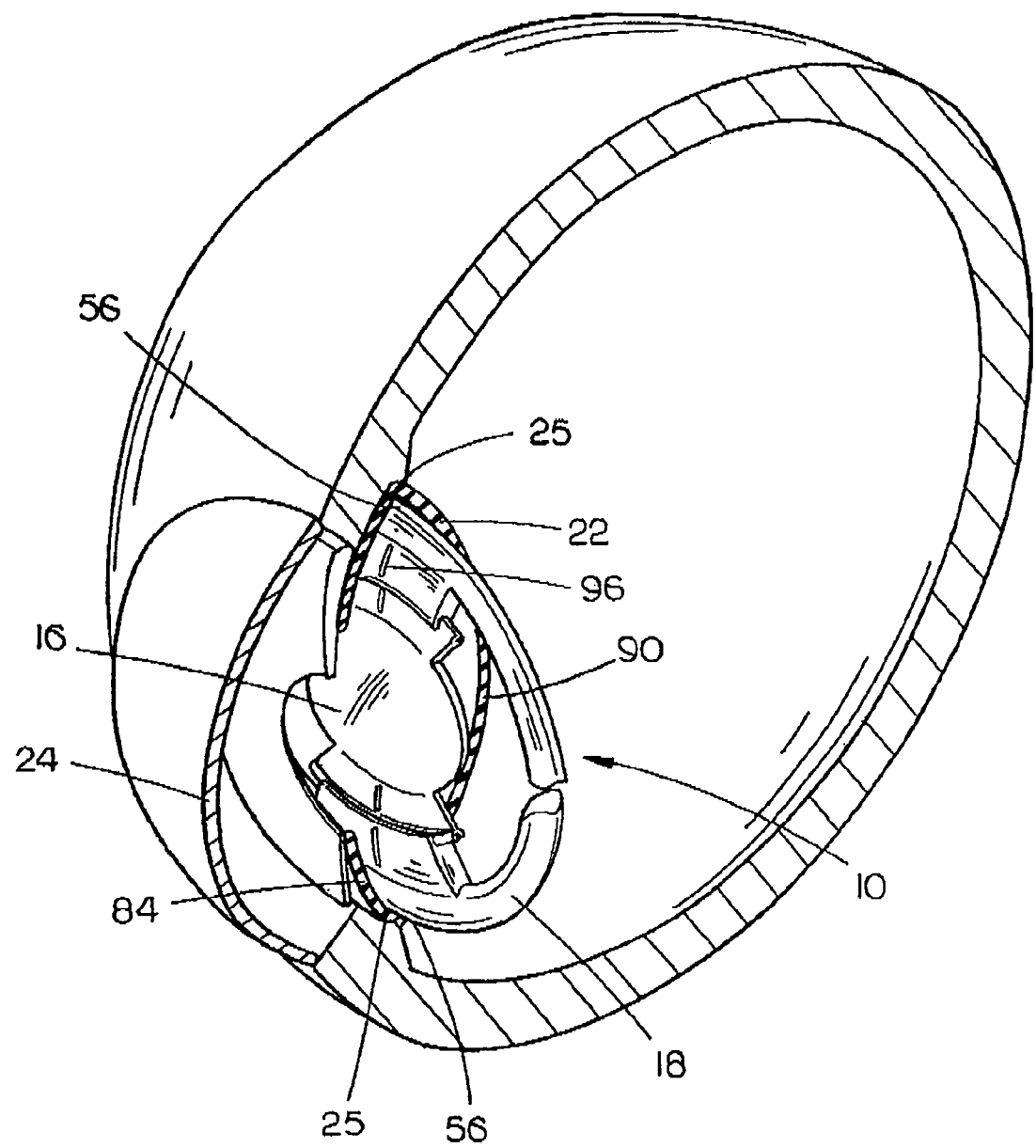
FIG. 9 is an anterior perspective view of a human eye in which the device of FIG. 7 has been placed in the capsular bag.
Figure 10:
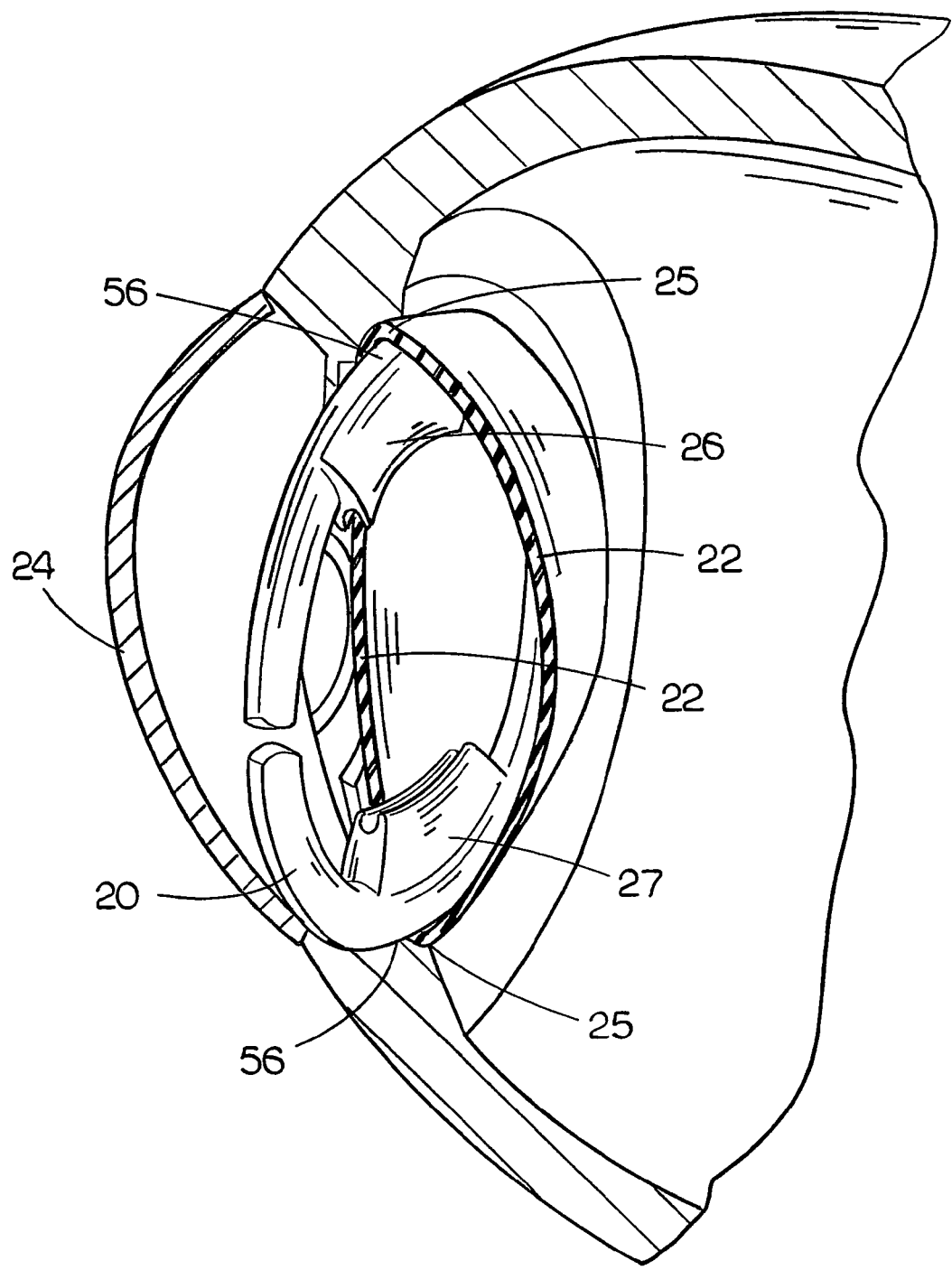
FIG. 10 is a posterior perspective view of a human eye in which the lens fixation platform of FIG. 1 has been placed in the capsular bag.
Figure 11:
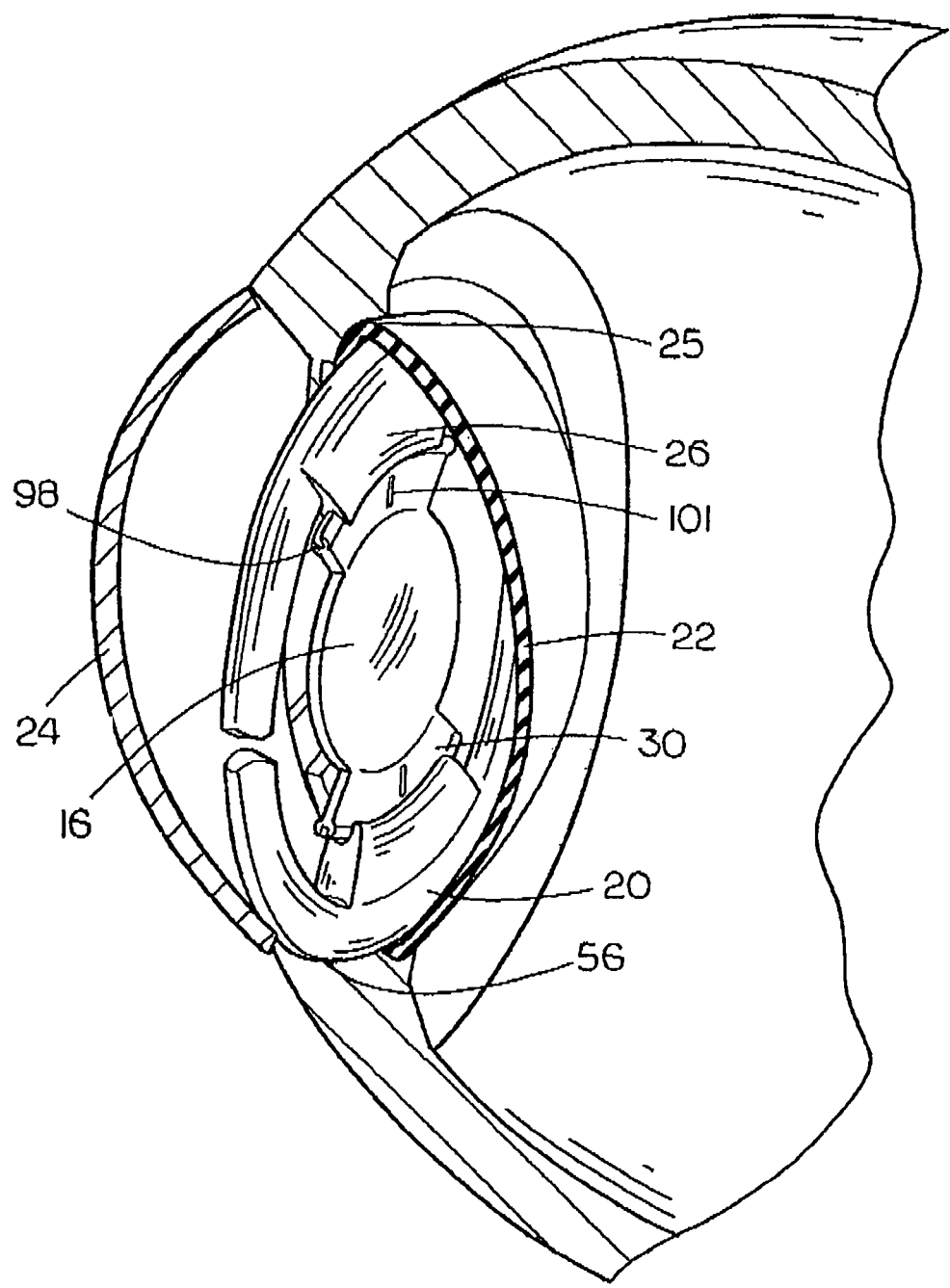
FIG. 11 is a posterior perspective view of a human eye in which the device of FIG. 7 has been placed in the capsular bag.

As best seen in FIGS. 7A&B the exchangeable intraocular lens device 10 of the present invention generally consists of a lens fixation platform ("platform") 12 and an intraocular lens ("IOL") 14 having an optic 16 with integral haptics 29 and 30. As described in more detail below, the integral haptics 29 and 30 releasably interconnect with the platform 12. The exchangeable intraocular lens device 10 is of an overall design analogous to that of a picture (the IOL) within a frame (the platform). The platform 12 is generally ring-shaped with an anterior surface 18 and a posterior surface 20, see FIG. 2B and is preferably made of flexible, bio-compatible, high-memory material such as acrylic, although the platform 12 may be made from any suitable flexible bio-compatible, high-memory material. The platform 12 is sized and shaped to fit securely, along its entire periphery, into the equatorial fornix 25 of the capsular bag 22 with the peripheral tip 56 of the platform 12 seated in the fornix 25 of the capsular bag 22, see FIGS. 9-11.

The seating of the platform 12 in the fornix 25 assists in estimation of the final resting position, i.e., the effective lens position ("ELP"), of the IOL 14 after attachment to the platform 12. The ability to delineate the plane in which the IOL 14 will reside after implantation will greatly improve the accuracy of intraocular lens power calculations over that achievable with prior art intraocular lenses and result in better uncorrected vision for patients. For example, with current technology, it has been determined that a 20.00 D intraocular lens that is axially displaced by 0.5 mm from the predicted effective lens position will result in approximately 1.00 D of error in the patient's stabilized postoperative refraction. (*IOL Power Calculations for Multifocal Lenses*, Holladay, bmctoday.net August 2007) Specifically, by better estimating the final ELP of the IOL 14, intraocular lens formulas for predicting the necessary power which utilize the ELP as a variable, e.g., Holladay 2 (Holladay Consulting, Inc., Bellaire, Tex.) will be more accurate. This will provide a particular advantage as the market penetration of multifocal/toric intraocular lenses increases.

The necessary sizing of the platform 12 can be determined based on art recognized measurements and other factors which are variable and best determined on an individual basis. For purposes of example only, the platform may have an outside diameter of between approximately 13 millimeters and 15 millimeters and an inside diameter (not including attachments) of between 10.5 millimeters and 12.5 millimeters. The distance between the containment grooves 42 on the attachments 26 and 27 ("cord length") can be approximately 8.4 millimeters. As described in more detail in Method of Use, other parameters may be considered to refine and optimize sizing so as to facilitate seating of the platform 12 into the fornix 25 of an individual patient's capsular bag. The size of the attachments 26 and 27 is preferably modified for each platform to have a consistent site (chord length) for attachment, for the IOL 14, independent of the diameter of the platform 12. Although modifying the size of the attachments 26 and 27 is preferred, modifying the size of the IOL 14 is within the scope of the invention.

Figure 3:
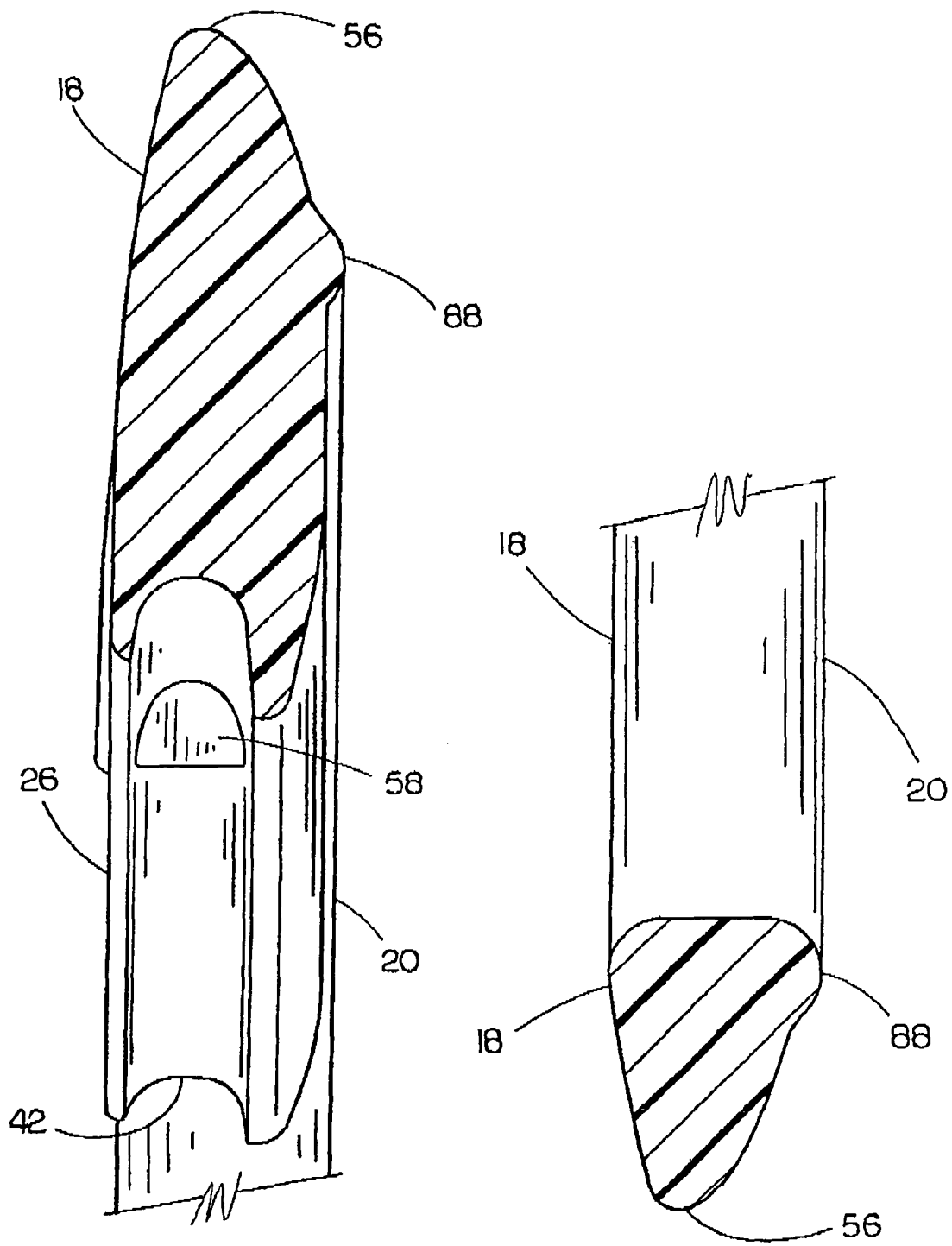
Figure 4:
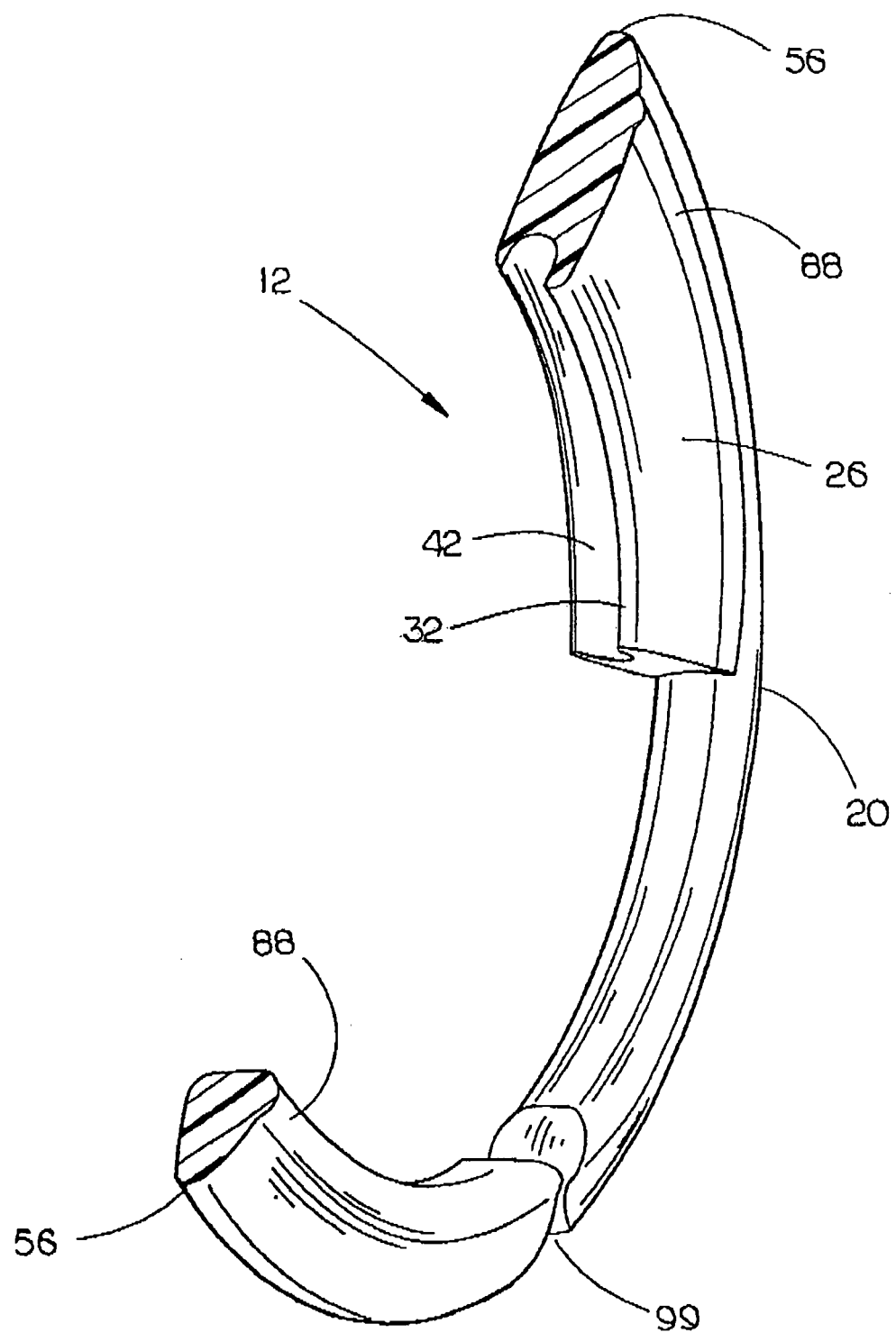
FIG. 4 is a perspective sectional posterior view.

As best shown in FIG. 3A, the anterior surface of platform 18 may be preferably convex to facilitate adherence and subsequent attachment, through fibrosis and shrinkage, to the anterior flap 84 of the capsular bag 22. As best shown in FIGS. 3A and B, the posterior surface of platform 20 preferably has a 1 millimeter raised circumferential rib 88 which contacts and engages the posterior capsular bag 90. Although the rib 88 can be of greater or lesser height of between approximately 0.5 millimeter and 1.5 millimeter. Additionally, it is within the scope of the present invention for there to be more than one posterior circumferential rib. The rib 88 functions to deter lens epithelial cell migration and thereby decrease the incidence of posterior capsular opacification ("PCO"). Current intraocular lens design utilizes a square posterior edge on the optic in an attempt to decrease epithelial cell migration. As a further advantage of the rounded surface of the circumferential rib 88 of the present invention it will be possible to use optics with gently rounded edges, and, thereby, improve optical quality and reduce unwanted optical aberrations, such as glare, negative dysphotopsias, peripheral arcs, inherent with use of square edge intraocular lens designs. Although the rib 88 is preferably rounded, it is within the scope of the present invention for the rib 88 to be square edged, or for the platform to not have a posterior rib.

Figure 1:
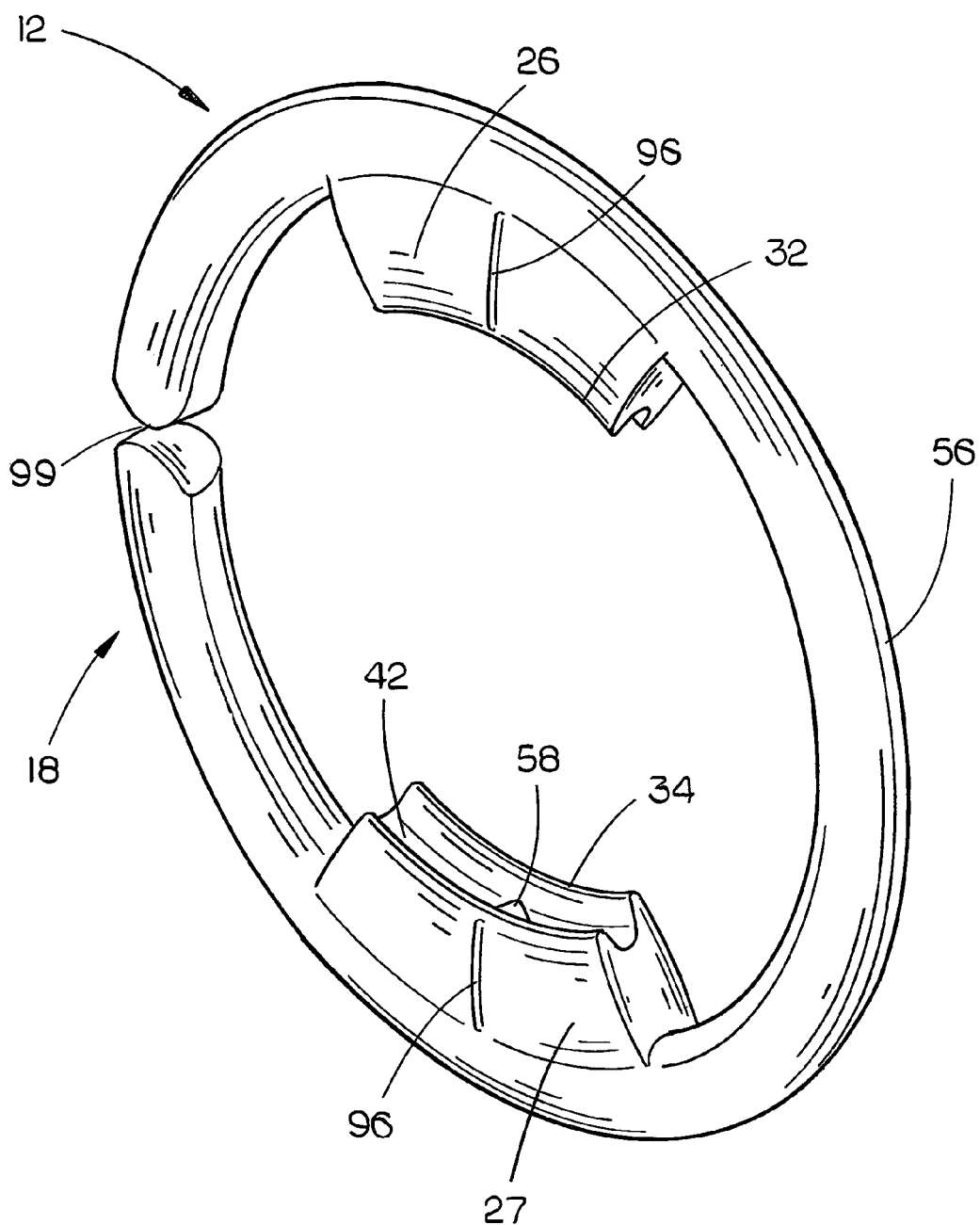
FIG. 1 is an anterior perspective view of the lens fixation platform.

As shown in FIG. 1, the platform 12 preferably has an attachment 26 at twelve o'clock and an attachment 27 at six o'clock. The attachments 26 and 27 project from the platform 12, inward toward the center axis 28, see FIG. 2B, of the platform 12. Although two are preferred, there may be more than two attachments on the platform 12. The inner most margins 32 and 34 of the attachments 26 and 27 are configured to releasably receive the haptics 29 and 30. Preferably, as shown in FIG. 1, the innermost margins 32 and 34 of the attachments 26 and 27 have a concave, u-shaped, containment groove 42 for receiving the peripheral margin 50 of the haptics 29 and 30. Although this configuration is preferred, it is also within the scope of the present invention for the margins of the attachments 32 and 34 to interconnect with the peripheral margins of the haptics 50 using a variety of releasable attachment mechanisms, such as a male and a female flange connection, tongue and groove junction, or the like.

Figure 8:
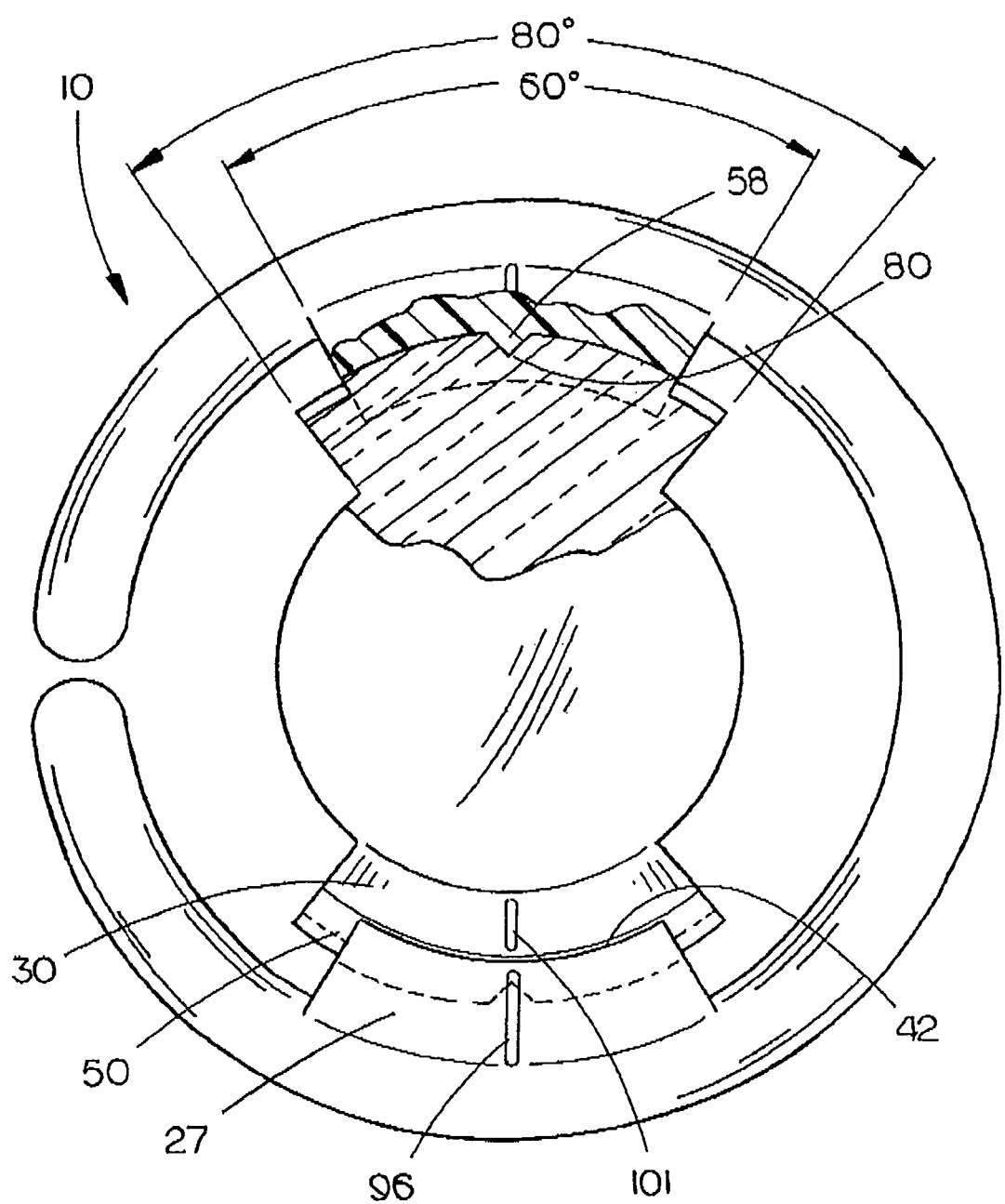
FIG. 8 is a front/anterior view of the assembled lens fixation platform and intraocular lens with partial sectional view.

The IOL 14 is preferably made of flexible silicone or acrylic and may be relatively less rigid than the platform 12, however, the IOL 14 may be of the same rigidity and furthermore, any suitable material as known in the art may be used. The optic 16 preferably has a standard diameter of approximately 6 millimeters. The optic 16 provides all of the desired corrective lens power. The maximum diameter of the IOL 14, including the haptics 29 and 30, is preferably approximately 8.5 millimeters, although other diameters are within the scope of the invention, as long as the IOL 14 fits securely into the platform 12. The integral haptics 29 and 30 extend outward approximately 1.25 millimeter from the periphery of the optic 16. The peripheral margins 50 of the haptics 29 and 30 engage the attachments 26 and 27 through approximately 60 degrees of arc to provide optimal contact between the containment grooves 42 of the platform 12 and the peripheral margins 50 of the haptics 29 and 30. FIG. 8. Although a 60 degree arc is preferred, it is within the scope of the invention for the peripheral margins of the haptics 29 and 30 to engage the attachments 26 and 27 through greater or lesser degree of arc, or for the haptics 29 and 30 and attachments 26 and 27 to not have curved margins. In summary, the haptics 29 and 30 are spaced, and the peripheral margins 50 of the haptics 29 and 30 are specifically adapted, to be received and fit securely and releaseably into the containment grooves 42 of the platform 12. As such, any appropriate intraocular lens, for example, monofocal, aspheric, presbyopic, multifocal, or toric intraocular lens, that has integral haptics 29 and 30 that are compatible with the attachments 26 and 27, may be used with the present invention.

The attachments 26 and 27 and haptics 29 and 30 are specifically designed to maximize the circumferential degree of attachment, and to minimize total engaged surface area between the haptics 29 and 30 and the attachments 26 and 27, see FIG. 8. The optimized surface area of contact between the haptics 29 and 30 and attachments 26 and 27 thereby decreases the possibility of the haptics 29 and 30 becoming locked by fibrosis and, further, greatly reduces the possibility of damage to the zonules of the eye upon removal. Another particular advantage of this relationship is the improved stabilization, planar (side-to-side) centration, and more accurate alignment of the IOL 14, while minimizing the resistance upon exclavation for surgical exchange of the IOL 14.

Preferably, the length of the peripheral margins 50 of the haptics 29 and 30 are greater than the length of the containment grooves 42, see FIG. 8. Also preferably, each end of the peripheral margins 50 have a disengagement notch 98, see FIG. 5, for instrument enclavation to facilitate separation of the IOL 14 from the platform 12 during removal of the IOL 14. Also within the scope of the present invention is for the peripheral margins 50 of the haptics 29 and 30 to not be greater in length than the containment grooves 42.

Preferably, the containment grooves 42 include a 'V' or other shaped projection 58, see FIG. 8, for locking into a corresponding recess 80 on the peripheral margins 50 of the haptics 29 and 30. The projection 58 is preferably designed to engage the recess 80 with a sensory snapping and thereby indicate engagement between the haptics 29 and 30 and containment grooves 42. The engagement of projection 58 and recess 80 further serves to guarantee centration and prevent rotation of the IOL 14 within the platform 12. Additionally, it is within the scope of the present invention for a projection to be located on the peripheral margins 50 and a recess to be located in the containment grooves 42, or for the containment grooves 42 to not have a projection or the peripheral margins 50 to not have a recess. The platform 12 and IOL 14 preferably have corresponding alignment guides 96 and 101, respectively, see FIG. 7A, to further assist with accuracy of alignment of the IOL 14 and to visually confirm the proper anterior/posterior orientation of the platform 12 and IOL 14 during surgery. Preferably, the alignment guides 96 on the platform 12 are located only on the anterior surface of the platform 18 so as to assist with proper orientation of the platform in the eye. Alignment guides 101 are preferably on the anterior surface of the IOL 14. It is also within the scope of the invention for there to be alignment guides on both sides or to have no alignment guides on IOL 14 and/or platform 12.

In a preferred embodiment, as best seen in FIG. 8, the exchangeable intraocular lens device 10 is assembled by inserting the peripheral margins 50 of the haptics 29 and 30 into the containment grooves 42 on the attachments 26 and 27, while positioning the alignment guides 96 on the platform 12 opposite the alignment guides 101 on the IOL 14 and fitting the projection 58 into the recess 80. The alignment guides 96 and 101 and projections 58 provide the particular advantages of assisting with and confirming proper placement of the IOL 14 in the platform 12.

Figure 5:
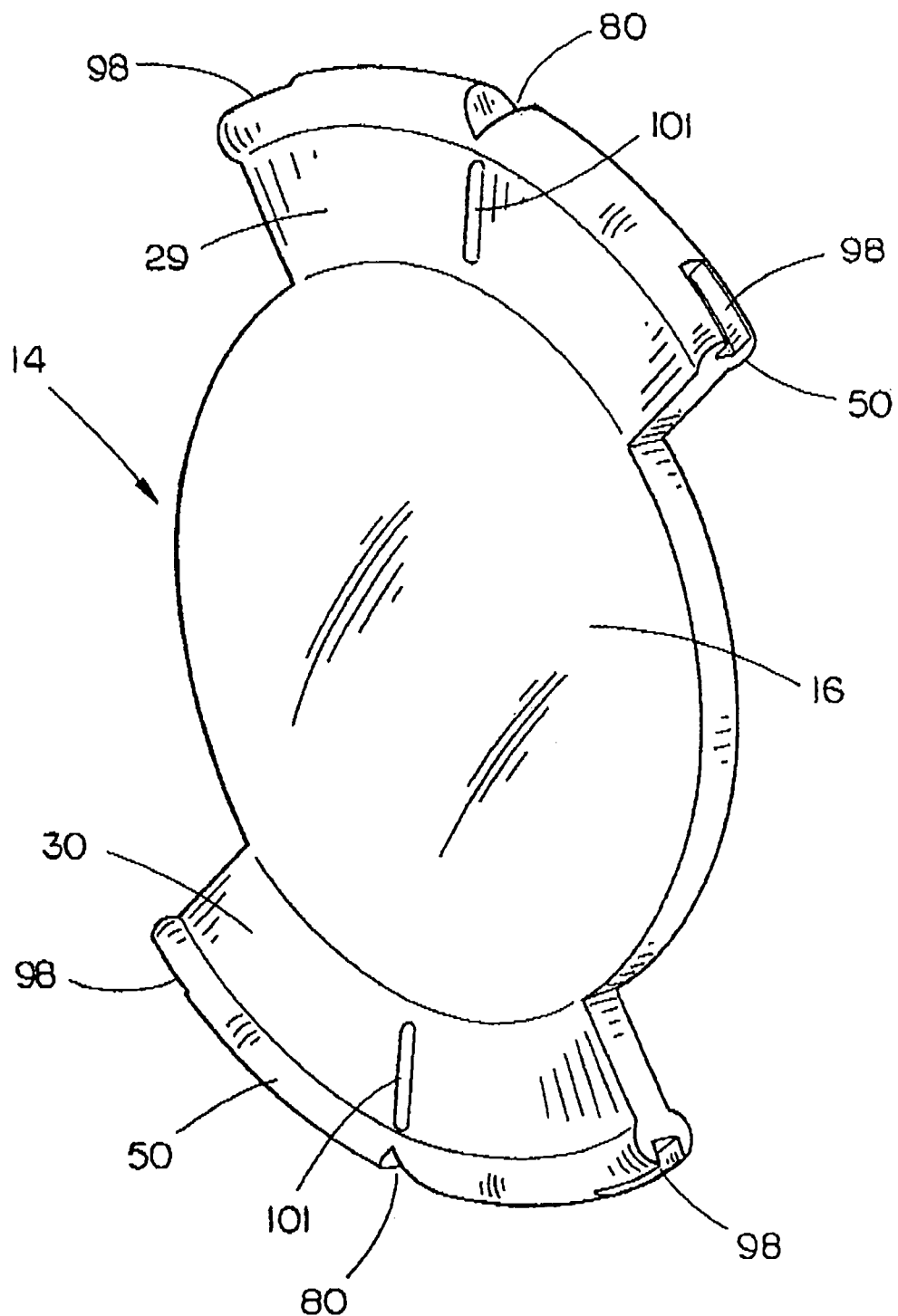
FIG. 5 is a perspective front/anterior view of the intraocular lens.

When desired to exchange the IOL, disengagement of the haptics 29 and 30 from the containment groove 42 can be facilitated, if necessary, with the use of any of the disengagement notches 98 located on opposite ends of the peripheral margins 50 of the haptics 29 and 30, as best shown in FIG. 5. While the disengagement notches 98 are the preferred configuration, a variety of other configurations may be used to facilitate disengagement of the IOL 14 from the attachments 26 and 27.

The ability to stabilize the platform 12 and disengage the haptics 29 and 30 using the disengagement notch 98 without the risk associated with rotating the IOL 14 during removal, provides a significant advantage. The desired replacement IOL 14 may be inserted, and appropriately placed and attached, as described more fully herein in Methods of Use. The exchange procedure may be repeated at any time to achieve desired visual results.

While specific embodiments have been shown and discussed, various modifications may of course be made, and the invention is not limited to the specific forms or arrangement of parts and steps described herein, except insofar as such limitations are included in the following claims. Further, it will be understood that certain features and sub-combinations are of utility and may be employed without reference to other features and sub-combinations. This is contemplated by and is within the scope of the present invention. For example, while the platform 12 as shown and described is a preferred embodiment, it will be appreciated that the exclusion of one or more of: the alignment guides 96 and 101; projection 82; recess 80; and disengagement notches 98, as specifically described above will not depart from the principal advantage of the present invention to provide an exchangeable intraocular lens device 10 having a permanently implanted lens fixation platform 12, and an IOL 14 which can be inserted and later removed for exchange.

Method of Use—Sizing of the Platform.

The platform 12 of the present invention is sized for optimal benefit to each individual patient's anatomy. Sizing of the platform 12 is performed preoperatively. Placement of an optimal size platform 12 in the eye helps facilitate maximum adherence of the platform 12 to the fornix 25 of the capsular bag 22. Furthermore, by placing the peripheral tip 56 of the platform 12 in the equator of the capsular bag 22, the effective lens position ("ELP") is more readily identified.

Proper sizing of the platform 12 depends on several art recognized measurements, such as, central corneal refractive power (keratometry readings), axial length (biometry), horizontal corneal diameter (horizontal white-to-white), anterior chamber depth, lenticular thickness, preoperative refraction, and age of the patient. Biometry measurements are taken to calculate the axial length. Using these parameters, the appropriate power of the IOL 14 and the proper platform 12 size is thereby determined for each eye.

The measured specific patient parameters provide the most accurate sizing data. However, for purposes of illustration, three approximate sizes for the platform 12 can be estimated depending on the axial length, white-to-white diameter, and anterior segment optical coherence tomography (OCT), as well as sonographic imaging. For example, a patient with an axial length less than 22.5 mm could receive a 13 mm diameter platform 12, with axial length of 22.5 to 24.0 mm could receive a 14 mm diameter platform 12, and a patient with an axial length of greater than 24.0 mm could receive a 15 mm diameter platform 12. These axial length estimates of appropriate platform 12 diameter are confirmed by biometry and anterior segment imaging.

Method of Use—Implantation of the Platform and Attachment of the IOL.

A standard, small incision of approximately 2.4 millimeters is made in the clear cornea 24. Preferably, a viscoelastic (dispersive/long chain) fluid is placed into the anterior chamber of the eye filling the capsular bag and protecting the corneal endothelium during surgery while distending the capsular bag. The platform 12 is then inserted through the same incision under the cushion of viscoelastic fluid into the capsular bag 22 of the eye using a holder/folder or any insertion device that can safely deliver the IOL 14 into the eye, as well known in the art. After insertion, the proper anterior/posterior orientation is achieved, and the platform 12 of the present invention will expand into the fornix 25 of the capsular bag, see FIG. 10. The platform 12 will then stabilize in the annular structure of the fornix 25. The biocompatible, material of which the platform 12 is composed will subsequently become permanently implanted and comprise the 'frame' in which the IOL 14 is attached, and from which the IOL 14 may later be removed.

When placed in the capsular bag 22, and confirmed visually, the platform 12 may be rotated to the appropriate axis (clock hour) as desired. The generally preferred axis is with the attachments 26 and 27 at 12 o'clock and 6 o'clock. However, when toric lenses are to be inserted, the platform 12 is rotated to the desired axis of astigmatism to be corrected by orienting the alignment guides 96 parallel with the axis of astigmatism. The ability to rotate the platform 12 prior to attachment of the IOL 14 provides a significant advantage. With this ability, a toric intraocular lens with a single axis of orientation can be manufactured and placed in the platform 12 that has been aligned with the desired axis, instead of having to manufacture toric lenses with different astigmatic power at every axis.

Use of any power of intraocular lens that has haptics 29 and 30 which are compatible with the attachments 26 and 27, is within the scope of the invention. For example, monofocal, aspheric, presbyopic, multifocal, or toric intraocular lens may be utilized. The IOL 14 is inserted into the anterior chamber through the same incision using those means known in the art, such as a holder/folder or other injection device. The IOL 14 is aligned with the platform 12 and proper alignment confirmed by the corresponding alignment guides 96 and 101. Under viscoelastic, the haptics 29 and 30 can then be 'popped' into place and securely attached to the attachments 26 and 27 with the projection 58 received in the recess 80. If desired, this may be accomplished using a Kuglan hook (Storz, St. Louis, Mo.), a microfinger hook or other device as known in the art. After attaching, the adherence of the IOL 14 to the platform 12, and adherence of the platform 12 within fornix 25, may be confirmed by attempted rotation of the IOL 14 clockwise and counterclockwise. Any rotation should be noted as a possible indication of inappropriate seating of the platform 12 or incomplete attachment of the haptics 29 and 30 to the platform 12. Appropriate sizing of the platform 12 will result in the expanded platform 12 securely resting in the equatorial fornix 25 of the capsular bag 22. The viscoelastic is then removed and replaced with a balanced salt solution. After viscoelastic removal, the axis of the assembled IOL 14 and platform 12 is visually confirmed. Thereafter, it is extremely unlikely that the platform 12 will rotate. The incision usually self-seals, however a stitch can be made if required.

Method of Use—Removal and Exchange of the IOL.

When exchange of IOL 14 is desired, exchange may be performed through a small size incision in the cornea 24, as for original implant, with minimal trauma and manipulation. After making the incision, the capsular bag 22 is filled with viscoelastic (dispursive/retentive) to protect the capsular bag 22 and endothelium during removal of the IOL 14. Adequate visco separation between the IOL 14 and capsular bag 22 must be achieved prior to insertion of an intraocular lens cutter. After confirmation of the intraocular lens cutters positioning, the optic 16 can be bisected with use of a standard intraocular lens scissors or cutter such as the Katena model KY5571 or KY5565 intraocular lens cutter or other device as known in the art for cutting and removing an intraocular lens. The intraocular lens cutter is then removed from the eye.

An intraocular lens hook, such as a Sinsky hook, microfinger or other device known in the art, may be inserted through the incision to engage the disengagement notch 98 and, by art recognized traction of the hook in the disengagement notch 98 and countertraction against the platform, to avoid pulling on the platform, the IOL 14 can be separated from the platform 12 and removed from the eye. In this manner, each haptic 29 and 30 may be carefully disengaged from the attachments 26 and 27.

The new IOL 14 may then be inserted, and appropriately placed and attached as discussed in detail above. This exchange procedure may be repeated when desired, depending on the patient's ocular status, and desired visual results.

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense.

What is claimed and desired to be secured by Letters Patent is as follows:

1. An intraocular lens device, comprising:
   a) a generally uniform diameter, ring-shaped lens platform adapted to expand along its entire circumference into an equatorial formix of an evacuated capsular bag of an eye, said platform comprising a break in the ring-shape to accommodate insertion into the eye, anterior and posterior surfaces, and a plurality of spaced attachments which extend inward toward the central axis of the platform, wherein the attachments have axial margins comprising a containment groove thereon, and further wherein said lens platform and the plurality of attachments are formed from biocompatible, flexible, high-memory material; and
   b) an exchangeable intraocular lens comprising anterior and posterior surfaces, an optic, and a plurality of integrally formed haptics, adapted to be placed within the containment groove so as to be releaseably attached to said attachments on the platform after the platform is implanted in the capsular bag.

2. The intraocular lens device of claim 1, wherein the attachments have inner margins comprising a projection there from.

3. The intraocular lens device of claim 1, wherein the haptics have peripheral margins adapted to attach to the containment grooves.

4. The intraocular lens device of claim 2, wherein the haptics have peripheral margins comprising a recess for engaging the projection.

5. The intraocular lens device of claim 1, further comprising an anterior alignment guide on the lens platform and a corresponding alignment guide on the haptic.

6. The intraocular lens device of claim 1, further comprising a circumferential rib on the posterior surface of the platform.

7. The intraocular lens device of claim 6, wherein the circumferential rib has a rounded surface.

8. The intraocular lens device of claim 1, wherein the haptics have peripheral margins and a disengagement notch on the peripheral margin of at least one of the haptics.

9. The intraocular lens device of claim 1, wherein the anterior surface of the platform is convex.

10. A generally uniform diameter, ring-shaped lens platform adapted to expand along its entire circumference into an equatorial formix of an evacuated capsular bag of an eye, said platform comprising a break in the ring-shape to accommodate insertion into the eye, anterior and posterior surfaces, and a plurality of spaced attachments which extend inward toward the central axis of the platform, wherein the attachments have axial margins comprising a containment groove thereon, and further wherein the lens platform and the plurality of attachments are formed from a biocompatible, flexible, high-memory material, said platform adapted to receive an intraocular lens for releasably attaching to the containment groove of the axial margins of the spaced attachments.

11. The platform of claim 10, wherein the attachments have inner margins comprising a projection there from.

12. The platform of claim 10, further comprising an anterior alignment guide.

13. An exchangeable intraocular lens adapted for placement in the platform of claim 10, comprising: anterior and posterior surfaces, an optic, and a plurality of integrally formed, peripherally spaced haptics adapted to be releaseably attached to said attachments on the platform after the platform is implanted in the capsular bag.

14. The intraocular lens of claim 13, wherein the haptics have peripheral margins adapted to attach to the axial margins of the attachments and, at least one which includes a disengagement notch.

15. A method of surgically inserting the intraocular lens device of claim 1, the method comprising:
   a) inserting the platform through an incision in the cornea of an eye and into an evacuated capsular bag;
   b) allowing the platform to expand into the capsular bag's equatorial formix;
   c) inserting the intraocular lens through the incision and into the capsular bag; and
   d) releaseably attaching the haptics of the intraocular lens to the attachments on the platform.

16. The method of claim 15, wherein the haptics comprise peripheral margins adapted to attach to the containment groove, and, wherein the method further comprises:
   e) attaching the peripheral margins to the containment groove.

17. The method of claim 16, wherein the containment groove has a projection there from, and the peripheral margins are adapted to attach to the containment groove, and said containment groove comprises a recess adapted to engage the projection, wherein the method further comprises:
   f) engaging the projection in the recess.

18. The method of claim 17, wherein the intraocular lens device further comprises an anterior alignment guide on the lens platform and a corresponding alignment guide on the haptic, and, wherein the method further comprises:
   g) aligning the corresponding alignment guide on the lens platform with the alignment guide on the haptic.

19. The method of claim 15, further comprising rotating the lens platform to an appropriate axis of astigmatism before attaching the intraocular lens.

* * * * *